(12) United States Patent
Kassab

(10) Patent No.: US 8,574,248 B2
(45) Date of Patent: Nov. 5, 2013

(54) CATHETER SYSTEM WITH BALLOON-MOUNTED PLAQUE-MODIFYING ELEMENTS

(75) Inventor: Elias H. Kassab, Grosse Pointe Shores, MI (US)

(73) Assignee: Kassab Kughn Endovascular Devices, Farmington, MI (US)

( * ) Notice: Subject to any disclaimer, the term of this patent is extended or adjusted under 35 U.S.C. 154(b) by 1 day.

(21) Appl. No.: 13/323,156

(22) Filed: Dec. 12, 2011

(65) Prior Publication Data

US 2013/0150874 A1 Jun. 13, 2013

(51) Int. Cl.
*A61B 17/22* (2006.01)

(52) U.S. Cl.
USPC ............................................ 606/159; 604/22

(58) Field of Classification Search
USPC ............ 606/159, 170, 194, 195, 192; 604/22, 604/96.01
See application file for complete search history.

(56) References Cited

U.S. PATENT DOCUMENTS

| | | | |
|---|---|---|---|
| 6,432,130 B1 * | 8/2002 | Hanson | 623/1.11 |
| 7,686,824 B2 * | 3/2010 | Konstantino et al. | 606/194 |
| 7,691,080 B2 | 4/2010 | Seward et al. | |
| 7,799,043 B2 | 9/2010 | O'Brien et al. | |
| 2002/0151924 A1 | 10/2002 | Shiber | |

* cited by examiner

*Primary Examiner* — Victor Nguyen
(74) *Attorney, Agent, or Firm* — Brooks Kushman P.C.

(57) ABSTRACT

A plaque-modifying balloon and method for use in an endovascular procedure includes an elongated balloon that defines a longitudinal axis and is inflatable from a first deflated configuration to a second radially expanded configuration. One or more plaque-modifying elements are mounted on the outside of the inflatable balloon. Optionally, a compressible sheath made of a relatively low durometer, flexible material is mounted on the balloon to cover the elements during transit of the plaque-modifying balloon to and from the treatment site.

3 Claims, 4 Drawing Sheets

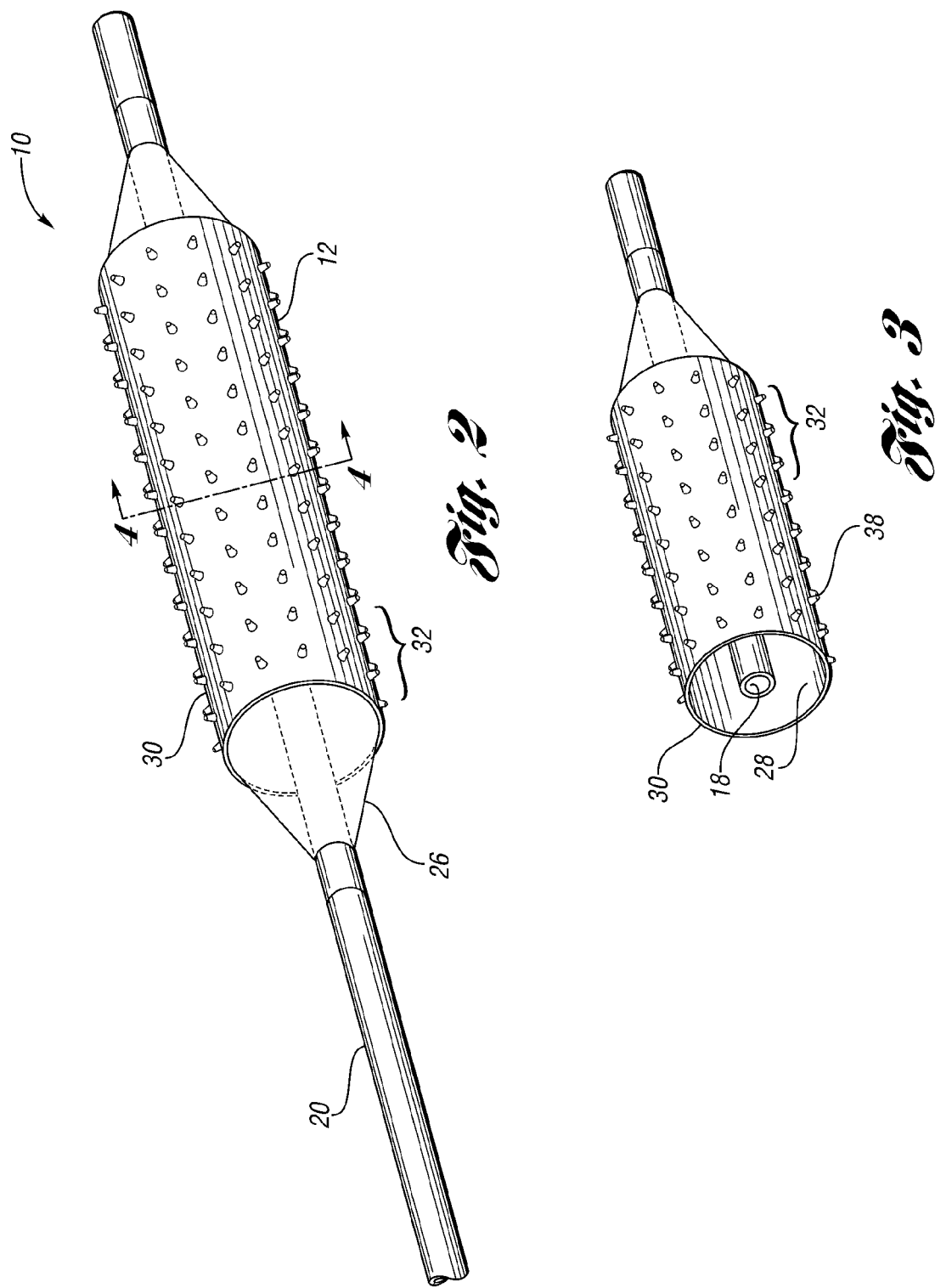

CATHETER SYSTEM WITH BALLOON-MOUNTED PLAQUE-MODIFYING ELEMENTS

BACKGROUND OF THE INVENTION (1) Field of the Invention

Percutaneous transluminal angioplasty (PTA) procedures can treat arterial disease. In such endovascular procedures, cutting balloons are sometimes considered as a treatment option for opening blocked coronary and peripheral vessels. Such balloons are sometimes configured so that balloon pressure is communicated to one or more cutting elements. Those elements may selectively cut stenosed vessel walls. In the hands of a skilled interventionist, PTA atherectomy procedures have sometimes reduced vessel recoil, lessened vessel tears and may have improved outcomes in comparison to traditional PTCA procedures.

Severing elements used in such balloons can for analysis be said to include an effective surface feature (e.g., an edge) that is capable of incising or scoring vessel walls with which they come into contact. But if suitable precautions are not taken, the incising elements can tear, cut or perforate the thin, fragile inflation balloon during assembly, handling or use. It is also possible that an unintended balloon rupture could damage the arterial wall. This may result in loss of inflation fluid into the patient's vasculature. Another problem may arise if an inadvertent or unwanted cutting occurs of adjacent perhaps healthy tissue as the cutting balloon is being positioned or withdrawn from the vasculature.

(2) Description of Related Art

A device with a cutting edge which is covered within the pleats of an expandable clover leaf-shaped tube is disclosed by Shiber in U.S. Publication No. US 2002/0151924. However, such designs may fail to protect a fragile balloon during installation of the cutting edges, even before the device is used in situ. In addition, because the blades are situated within the balloon folds, creased portions of the balloon may be exposed to the blades when the device is navigated by twisting, turning and bending through narrow tortuous vasculature passageways.

The following references, among others, were considered before filing this application: U.S. Pat. Nos. 7,686,824; 7,799,043; and 7,691,080.

BRIEF SUMMARY OF THE INVENTION

Against this background, it would be advantageous to provide an assembly of plaque-modifying elements that are urged into contact with stenosed vessel walls and weaken those hardened portions as well as calcific plaques by creating and propagating localized fissures.

Yet other desires include providing a catheter system with an assembly of plaque-modifying elements that extend from an inflatable balloon which is easy to use by surgeons of varying skill levels, is straightforward to make and is comparatively cost-effective.

One aspect of the invention focuses on a plaque-modifying catheter system that includes an inflatable balloon which is provided with plaque-modifying elements that alter the surface and sub-surface characteristics of stenotic tissue at a treatment site in a vessel of a patient. For discussion and analysis, an embodiment of a catheter system falling within the scope of the present disclosure has an elongated balloon that defines a longitudinal axis. The balloon is inflatable from a first deflated configuration through intermediate second configurations to a third radially expanded configuration.

In some embodiments, the balloon includes one or more stiff pedestals or footpads ("plaque-modifying elements") that are brought into contact with plaque on vessel walls during inflation. For example, the pedestals could be considered as a punch or tool with a head that is circular, rounded ("domed"), x-shaped, star-shaped, polygonal, and the like. Its constituent material may include a hardened polymer. In some embodiments, the array of plaque-modifying elements is oriented longitudinally and mounted on the outside of the inflatable balloon.

When the inflatable balloon is in the radially expanded configuration, at least some of the pedestals are urged outwardly radially by the inflatable balloon so that they are capable of fracturing hardened tissue (soft plaque, as well as calcific plaques).

The balloon may further include on its outer surface one or more mounting pads that secure the pedestals to the balloons. For example, some of the pedestals may extend from an associated mounting pad that is affixed to the outer surface of the inflatable balloon.

Optionally, the plaque-modifying balloon system includes one or more sheaths that are made of a relatively low durometer, flexible material. Functionally, if used, each sheath protects the vasculature from an operative surface feature of a plaque-modifying element during transit of the balloon to and from the treatment site.

BRIEF DESCRIPTION OF THE SEVERAL VIEWS OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2 is a perspective view of one embodiment of the catheter system (without a covering sheath);

FIG. 3 is perspective partially sectioned view of the embodiment of a plaque-modifying balloon system depicted in FIG. 2;

DETAILED DESCRIPTION OF THE INVENTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
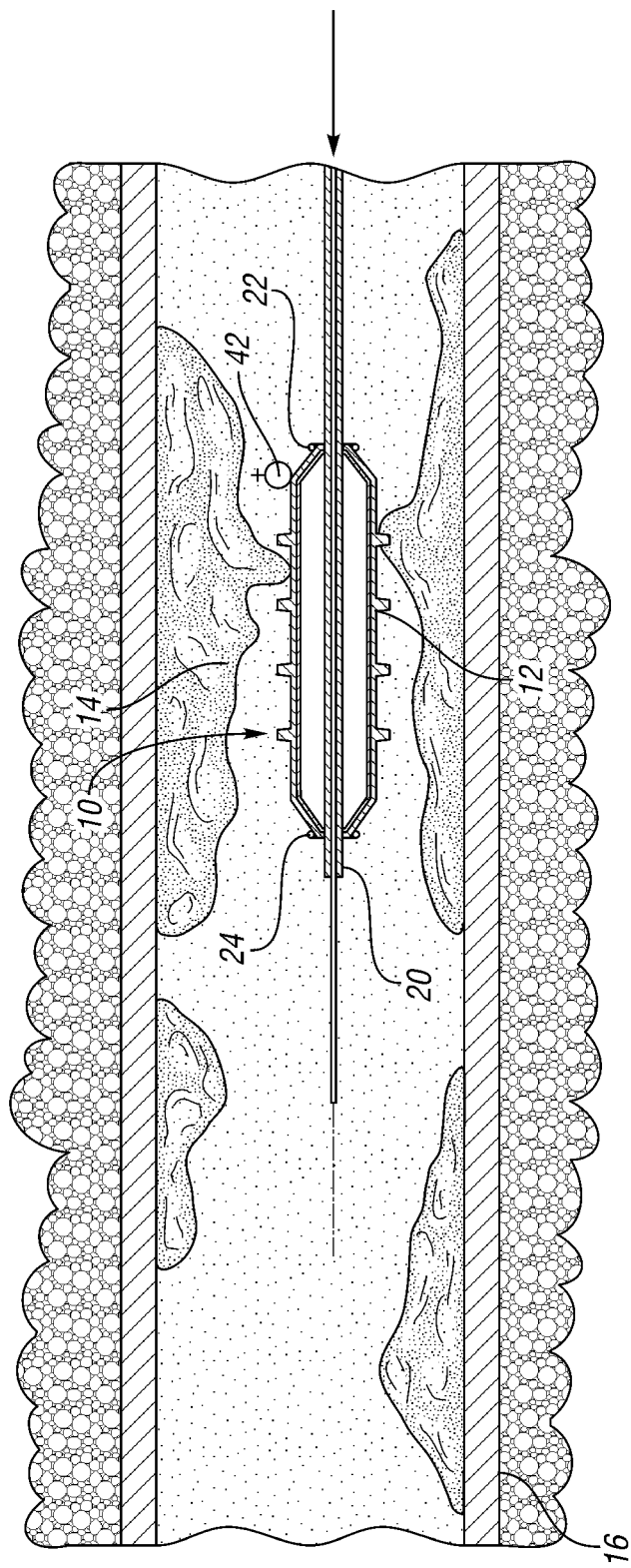
FIG. 1 is a simplified, longitudinal cross sectional schematic view of a catheter system having an array of plaque-modifying elements operatively positioned in the body of a patient.

Referring initially to FIG. 1, a plaque-modifying catheter system 10 is shown with an expansible balloon 12 that supports plaque-modifying elements 32. The system 10 enables a surgeon to perform an endovascular procedure in which a catheter with a deflated balloon surrounding it is inserted percutaneously into a blood vessel (e.g., a femoral artery) to treat vascular disease.

More specifically, the catheter system 10 is depicted as being positioned to treat a lesion 14 in an artery 16 such as but not limited to a coronary, renal, popliteal or femoral artery, the aorta or other artery. But those skilled in the art will recognize that the use of the catheter system 10 as herein described is not limited to treatment of a specific artery. Instead it can be deployed in vascular conduits and other ductal systems throughout the human body.

In FIGS. 1-4, there is depicted one embodiment of a plaque-modifying catheter system 10 with an open inner lumen 18. In that embodiment, the system 10 has a catheter (tube) 20 with a proximal end 22 and a distal end 24. As used herein, "proximal" is used in relation to the surgeon. The inner lumen 18 extends between the proximal 22 and distal 24 ends so that a medical device or fluid may pass through the lumen 18 without interruption or interference. If desired, the disclosed invention could be used as a blood perfusion balloon catheter such as that disclosed in U.S. Pat. No. 5,370,617. Such catheters can be used in administering treatments to relieve stenotic regions within a body lumen while maintaining blood flow past the dilation balloons. Perfusion ports in one example can be provided in both a guide wire lumen and in a bypass lumen in order to provide increased blood flow. Abstract, '617 patent.

Thus, the plaque-modifying balloon 12 includes an expandable balloon 26 (FIG. 4) that is located proximate to and circumscribes at least the distal end region 22 of the catheter 20. The expandable balloon 26 encapsulates a pressurizing fluid (such as a saline solution or nitrous oxide) in a chamber 28 formed between the catheter 20 and the balloon 26, which causes the balloon 26 to inflate. The balloon 26 has an outer surface 30 which may optionally at least partially have a dry coating. The pressurizing fluid is delivered by means for pressurizing, maintaining and deflating the chamber 28 formed between the catheter and the balloon (such as a pump in communication with an activator for imparting a rapid rise in pressure).

An assembly of plaque-modifying elements 32 is mounted on at least a part of the outer surface 30 of the balloon 26. Without being bound to any theory of operation, the modifying elements 32 are thought to break collagen and distend elastin in the intima and media of a vessel wall 16, thereby weakening the intima and media and superimposing (by, for example "stamping" or "embossing" or "fracturing") a pattern of weakened areas in the vessel wall 16. Such weakened areas may allow the vessel wall 16 to become more flexible, to bend and to distend radially.

In one treatment protocol, it is envisioned that the step of pressurizing the balloon is completed in about 1-5 seconds and the step of depressurizing the balloon is completed in a similar time. Optionally the step of contacting the balloon with a vessel wall to be treated is completed over a dwell time of about 1-5 minutes or longer if desired.

In one embodiment, at least some of the modifying elements 32 are supported from a base 34 extending from the outer surface 30 of the balloon 26. Extending outwardly from the base 34 is a shaft 36. A plaque-modifying tip 38 is situated atop the shaft 36. The plaque-modifying tip 38 has a cross section geometry selected from the group consisting of a polygon, an oval, a circle, a dome, an ellipse, an "x" shape, a star shape and a "y" shape.

In an embodiment, optionally, a retractable sheath 40 at least partially covers the modifying elements 32 as the catheter system 10 is maneuvered through a tortuous vasculature. The sheath 40 can be retracted to expose at least a part of the plaque-modifying assembly 32 when the assembly 32 is juxtaposed with a site to be treated. If desired, the sheath 40 can be repositioned to cover the plaque-modifying assembly 32 before the catheter system 10 is withdrawn.

Not shown in communication with the balloon 26 are one or more conventional fluid ports for pressurization and relief of the chamber 28 between the catheter 20 and the balloon 26. It will be appreciated that the proximal portion 22 of the catheter 20 is connected to the distal end 26 of an inflation mechanism or the means for inflation 42 (FIG. 1). Typically, the inflatable balloon 26 is made of a polymeric material such as polyethylene terephthalate (PET) or nylon and its outside diameter is about 6-8 French.

Figure 4:
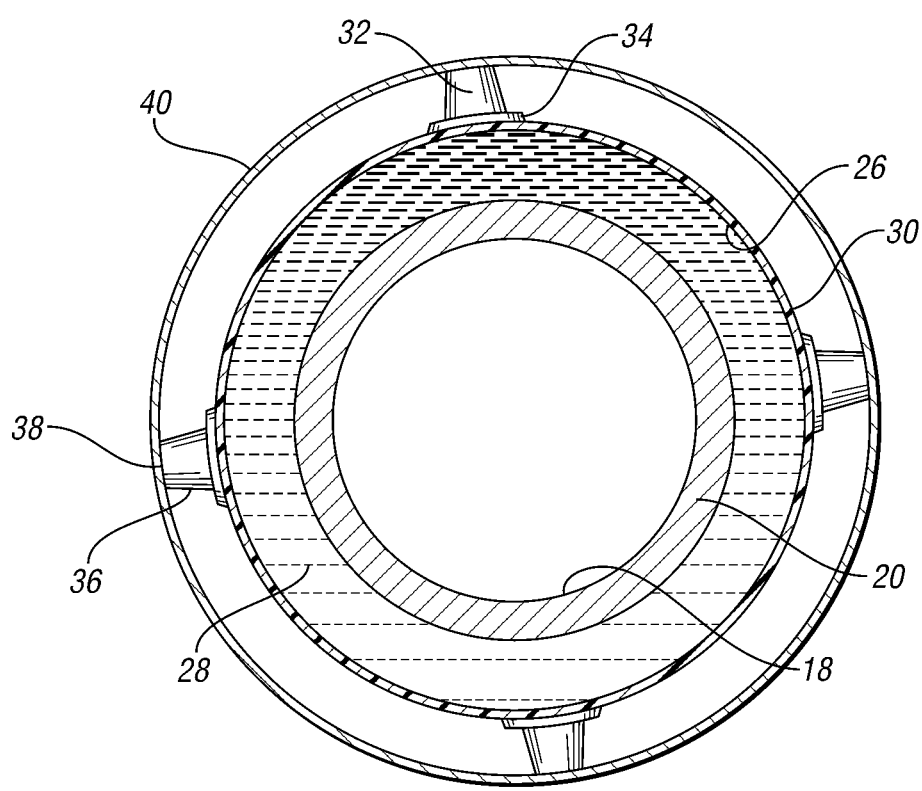
FIG. 4 is a cross sectional view of the balloon system of FIGS. 1-3 shown after the balloon has been inflated to urge plaque-modifying elements radially outwardly before sheath removal.

As best seen in FIG. 4, the inflatable balloon 26 can be thought of as having an outer surface 30 and an opposed inner surface 46 that surrounds an inflation volume or chamber 28 that can be infused with a medical grade fluid to expand the inflatable balloon 26. It will be appreciated that an inflation device 42 (not shown) may include a syringe that can be activated to pump the medical grade fluid (such as a saline solution) to expand the inflatable balloon 26.

In FIGS. 1-4, the plaque-modifying elements 32 may assume various alternative forms. These include tips 38 that are circular, rounded ("domed"), x-shaped, star-shaped, polygonal, and the like in a variety of configurations, e.g., an array of longitudinally or laterally spaced or aligned sets, as shown in FIGS. 2-3. As seen in FIG. 4, in one embodiment, the modifying elements 32 are distributed around the circumference 30 of an operative section of the inflatable balloon 26. Typically, at least some of the modifying elements 32 are made of a medical grade material such as a hard plastic like polytetrafluoroethylene (PTFE).

As best seen in FIG. 4, a portion of at least some of the modifying elements 32 extend from associated mounting pads or bases 34 that are secured to an outside surface 30 of the balloon 26. Typically, each mounting pad 34 is made of a relatively flexible polymeric material such as polyurethane and is bonded (e.g. heat bonded or adhesively bonded) to the outer surface 30 of the inflatable balloon 12. It can further be seen that each element 32 extends from its associated mounting pad 34 to an operative tip 38 that is capable of modifying the plaque with which it is urged into contact upon balloon inflation. The process is analogous to fracturing the plaque and causing a modified surface that in some cases may resemble the fractured windshield of an automobile.

It can be further seen that the tip 38 of each plaque-modifying element 32 extends in a radial direction ("height") which on average amounts to a distance "X" from the outer surface 30 of the balloon 26. The rise and fall ("pulse") during balloon compression and decompression occurs over an average distance "x". For the embodiment shown in FIGS. 3 and 4, the plaque-modifying elements 32 are preferably bonded to the inflatable balloon 26. This structure limits the amount of a given element that can sink into ambient plaque, by analogy to a depth gauge.

Regardless of whether a sheath is deployed, it is sometimes preferable that the plaque modifying elements 32 closer to the distal end 24 of the balloon 26 are closer to the balloon surface elements 32 that lie closer to the proximal end 22 of the balloon 12 to facilitate insertion of the catheter system 10 into the vasculature.

In alternate embodiments, the plaque-modifying elements 32 are not too tightly located and are spaced apart. In some embodiments the average spacing between adjacent elements is at least 3 times the height of the tip above the outer surface of the balloon. This geometry permits navigation of the catheter system 10 around abrupt turns in the vasculature without adjacent elements 32 interfering with each other.

The plaque-modifying elements are optionally aligned in longitudinally oriented rows on an outside surface of the balloon. In some embodiments, the plaque-modifying elements are aligned in laterally oriented rows on an outside surface of the balloon. Alternatively, the plaque-modifying elements are staggered so that an element in a row lies longitudinally between adjacent elements in a neighboring lateral row.

The functionality of one sheath embodiment 40 can be appreciated with reference to FIG. 4. As shown, the optional sheath 40, if deployed, protects the effective tips 38 of plaque-modifying elements 32 during transit of the balloon 26 and plaque-modifying elements 32 to the treatment site. After the system 10 is positioned at the treatment site and before the balloon 26 is expanded, the sheath 40 (if present) is withdrawn. The plaque-modifying elements 32 make their first contact with the tissue 14 (see FIG. 1). Once contact has been established between the tissue 14 and the plaque-modifying elements 32, further pressurization over a short period of time of the inflatable balloon 26 causes the elements 32 to pulse outwardly radially for tissue modification. Plaque modification arises from localized weakening by fracture of for example calcified areas. Not only does fracture engender fissure formation (thereby weakening the fissured area), but it also reduces the stiffness of plaque-lined vessel walls while augmenting the surface area over which chemical reaction occurs if a pharmaceutically effective drug is delivered thereto. If desired, pressure can be applied quickly once, like a single hammer blow to a sheet of ice. Alternatively, pressure can be administered pulsatingly, like a jack hammer. Optionally the means for pressurizing 42 includes a control mechanism that allows the surgeon to administer either or both modes of pressure application.

Figure 5:
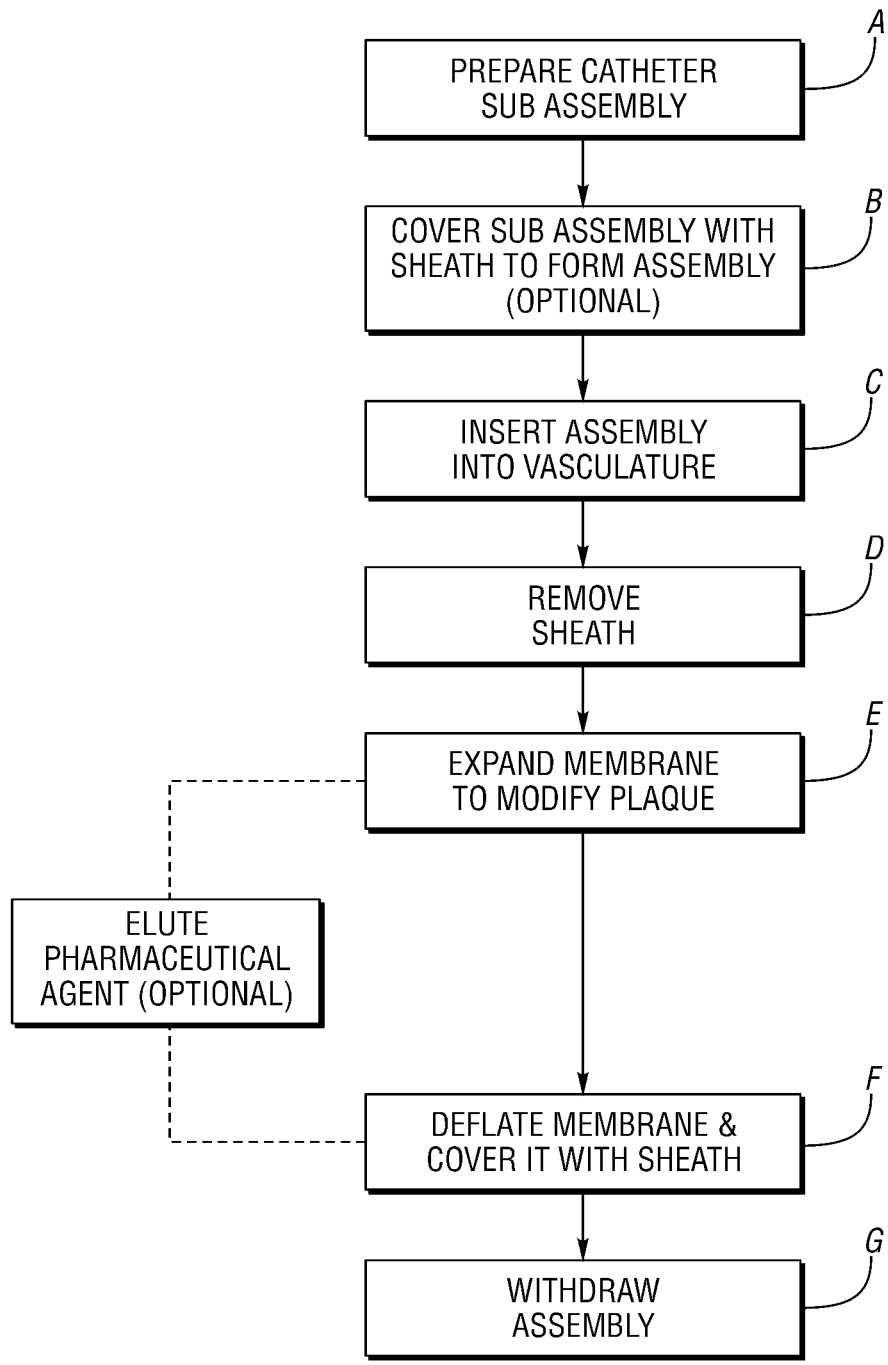
FIG. 5 illustrates method steps that exemplify how the catheter system is used.

FIG. 5 illustrates a series of method steps that can be followed in practicing one aspect of the disclosed endovascular protocol.

The steps include:

A. Prepare a catheter subassembly. This step involves connecting a catheter which is covered at least partially somewhere but not necessarily completely between its intermediate region and distal end by an expansible balloon to an external source of fluid pressure. The source may optionally be provided with a pulsating means so that balloon expansion can be controlled and (if desired) affected rapidly, thereby creating a pulsating or hammer-like impact to a stenosed region. Optionally, pressure could be increased more slowly and stopped.

B. Optionally cover the catheter subassembly with a sheath to form a catheter assembly. When used, the sheath protects potentially healthy vessel walls from abrasion by unprotected plaque-modifying elements.

C. Insert the assembly into the vasculature. One insertion site is the femoral artery, although other sites may be used. Following insertion, the assembly is carefully pushed along the tortuous vascular passageways until it is juxtaposed with an anatomical site to be treated.

D. If present, the sheath may then be removed, thereby exposing the plaque-modifying elements.

E. The balloon is then expanded by the application of fluid pressure. If used, a saline solution or nitrous oxide, for example, can be first used to flood a chamber between the outside of the catheter and the inside of the balloon, thereby expanding it. If desired, a shockwave can be propagated through the relatively incompressible fluid so that a punching effect on the stenosed vessel wall can be created by rapidly moving plaque-modifying elements. Optionally:
1. pharmaceutical agent may be delivered by microchannels extending through the plaque-modifying elements to the stenosed region either before or after fracture; or
2. the drug may be bonded to the balloon wall and by contiguity eluted into the vessel (e.g., Paclitaxel is lipophilic and rapidly reacts within 60 seconds with the vessel wall).

F. The balloon may then be deflated by evacuating the pressurizing fluid before the deflated balloon is covered with the sheath. The assembly may then be withdrawn in such a way that the plaque-modifying elements do not interfere with potentially healthy regions of the vasculature.

It will be appreciated that plaque-lined vessel walls following treatment become more compliant and therefore can bend, thereby responding to rather than resisting pulsating blood pressure.

Without being bound by a particular theory of operation, the Applicant anticipates that effective deployment of the disclosed system may usefully smoothen the arterial walls without leaving scars. Rather, the modified surface tends to be compliant, by analogy to perforated paper that extends rather than tears upon being subjected to stretching forces.

Preferably, the depth of plaque-modification should not exceed about one-half of the thickness of the vessel wall. Flexibility is thereby provided to a plaque-lined arterial wall which can open in response to blood pressure and flow.

Thus, there has been disclosed a plaque-modifying catheter system which can be used effectively upon single insertion and single delivery.

While the particular plaque-modifying elements 32 as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

| LIST OF REFERENCE NUMERALS | |
|---|---|
| 10 | Catheter system |
| 12 | Balloon |
| 14 | Lesion |
| 16 | Artery |
| 18 | Inner lumen (of 20) |
| 20 | Catheter (tube) |
| 22 | Proximal end (of 20) |
| 24 | Distal end |

-continued

LIST OF REFERENCE NUMERALS

| 26 | Balloon |
| 28 | Pressurizing fluid |
| 30 | Outer surface (of 26) |
| 32 | Assembly of plaque - modifying elements |
| 34 | Base (of 32) |
| 36 | Shaft |
| 38 | Tip |
| 40 | Sheath |
| 42 | Inflation device |
| 46 | Inner surface (of 26) |

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A plaque-modifying catheter system comprising:
    a catheter having a proximal end, a distal end and an intermediate section therebetween;
    an inner lumen between the proximal and distal ends through which a medical device or fluid may pass without interruption or interference;
    an expandable balloon located between the proximal and distal ends of the catheter and circumscribing at least the intermediate section of the catheter, the balloon receiving a pressurizing fluid between the catheter and the balloon which causes the balloon to inflate, the balloon having an outer surface; and
    an assembly of plaque-modifying elements mounted on at least a part of the outer surface of the balloon, wherein the plaque-modifying elements are separated from each other before, during, and after balloon expansion, thereby creating an array of weakened areas in a vessel wall when the plaque-modifying elements are urged into contact with the vessel wall by the pressurizing fluid inflating the outer surface of the balloon and the plaque-modifying elements impinging on the vessel wall, thereby fracturing hardened tissue and creating the weakened areas therein, at least some of the plaque-modifying elements having a tip situated atop a plaque-modifying element, the tip having a cross section geometry selected from the group consisting of, an oval, a circle, a dome, an ellipse, an "x" shape, a star shape and a "y" shape.

2. The plaque-modifying catheter system of claim 1, further including:
    a retractable sheath that at least partially covers the plaque-modifying elements as the catheter system is maneuvered through a tortuous vasculature, the sheath being retracted to expose at least a part of the plaque-modifying assembly when the assembly is juxtaposed with a site to be treated, and is repositioned to cover the plaque-modifying assembly before the catheter system is withdrawn.

3. The plaque-modifying catheter system of claim 1, wherein:
    the assembly of plaque-modifying elements is normally in a radially collapsed configuration and displaceable outwardly to a radially expanded configuration, wherein the assembly returns to its radially collapsed configuration when the balloon is deflated;
    wherein the plaque-modifying elements are adapted to crack hardened stenotic material when the balloon is expanded in a blood vessel lumen; and
    wherein said one or more plaque-modifying elements are disposed between the proximal and distal ends of the catheter proximate a distal end region, the balloon being at least partially covered by a sheath that extends over the elements as the balloon is inflated and deflated.

* * * * *